(12) United States Patent
Shibata et al.

(10) Patent No.: US 6,794,556 B2
(45) Date of Patent: Sep. 21, 2004

(54) LIQUID ABSORBENT

(75) Inventors: Akira Shibata, Kagawa (JP); Masahiko Shikatani, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/935,728

(22) Filed: Aug. 23, 2001

(65) Prior Publication Data
US 2002/0052586 A1 May 2, 2002

(30) Foreign Application Priority Data
Sep. 1, 2000 (JP) ........................................ 2000-265485

(51) Int. Cl.[7] ................................................ A61F 13/15
(52) U.S. Cl. ...................................... 604/372; 604/378
(58) Field of Search ................................ 604/378, 367, 604/372; 428/315.9

(56) References Cited

U.S. PATENT DOCUMENTS

| | | | | |
|---|---|---|---|---|
| 3,929,135 A | * | 12/1975 | Thompson | 128/287 |
| 5,006,394 A | * | 4/1991 | Baird | 428/138 |
| 5,591,149 A | * | 1/1997 | Cree et al. | 604/368 |
| 5,914,184 A | * | 6/1999 | Morman | 428/315.9 |
| 6,132,410 A | * | 10/2000 | Van Gompel et al. | 604/358 |
| 6,218,593 B1 | * | 4/2001 | Torimae et al. | 604/365 |
| 6,274,232 B1 | * | 8/2001 | Otten et al. | 428/304.4 |
| 6,548,158 B2 | * | 4/2003 | Mizutani et al. | 428/323 |

FOREIGN PATENT DOCUMENTS

| | | | | |
|---|---|---|---|---|
| DE | 4016348 | | 11/1991 | ............ B32B/5/02 |
| EP | 0320314 | | 6/1989 | ........... B32B/27/12 |
| GB | 2235878 A | * | 3/1991 | ........... A61F/13/46 |
| JP | 63-139728 | | 6/1988 | |
| JP | 1990-078623 | | 1/1990 | ............ A23B/4/00 |
| JP | 07-241944 | | 9/1995 | |
| JP | 09-086569 | | 3/1997 | |
| JP | 09086569 | | 3/1997 | ........... B65D/81/26 |
| JP | 1993-140070 | | 7/2000 | ........... B32B/27/12 |

* cited by examiner

Primary Examiner—John J. Calvert
Assistant Examiner—C. Lynne Anderson
(74) Attorney, Agent, or Firm—Darby & Darby

(57) ABSTRACT

Provided is a liquid absorbent including a liquid-absorbing layer of synthetic fibers by hydrophilic treatment and/or hydrophilic fibers; and a synthetic resin film bonded to a surface of the liquid-absorbing layer and having a large number of through-holes. The synthetic resin film is laminated on the surface of the liquid-absorbing layer through melt extrusion thereon, and the liquid-absorbing layer and the synthetic resin film are airtightly bonded to each other.

3 Claims, 2 Drawing Sheets

LIQUID ABSORBENT

BACKGROUND OF THE INVENTION

1. Field of the Invention

The present invention relates to a liquid absorbent which is used under dripping foods as a food drip-absorbing sheet, and is also usable in sanitary napkins or pantiliners.

2. Description of the Related Art

When retailed in the stores or the like, perishable foods, especially seafood and meat are laid on trays, and then the trays and perishable foods laid on the trays are individually covered with a wrapping film.

While laid on trays, juices or other liquids (these are referred to as "drips" hereinafter) exude from the foods such as seafood and meat therein. If such drips accumulate in trays, the appearances of the foods in showcases tend to be degraded. In addition, if the drips are kept in long contact with such perishable food, this provides an environment supportive of the growth of bacteria. Especially for meat, if the interface between meat and trays is not aerated, the surface of the meat airtightly kept in contact with the trays will be browned due to discoloration. Accordingly, breathable, liquid absorbent capable of absorbing drips of foods is disposed between trays and foods.

As a liquid absorbent of this type, a liquid absorbent comprising a liquid-absorbing layer of fibers and a liquid-pervious synthetic resin film bonded to the surface of the liquid-absorbing layer is well known in the art. For bonding the liquid-absorbing layer and the synthetic resin film, for example, a resin adhesive is used in Japanese Unexamined Patent Publication (Kokai) No. Heisei 7-241944. Further, in Japanese Examined Patent Publication (Kokoku) No. Heisei 4-70983, a synthetic resin film combined with a liquid-absorbing layer is perforated with hot needles to melt around the perforations formed through the film, and the film is thus adhered to the liquid-absorbing layer via the melted resin around the perforations. Still further, in Japanese Unexamined Patent Publication (Kokai) No. Heisei 9-86569, a mesh film of synthetic resin is heat sealed with a liquid-absorbing layer.

The conventional liquid absorbents set forth above, however, possess certain disadvantages. Specifically, as disclosed in Japanese Unexamined Patent Publication (Kokai) No. Heisei 7-241944, the liquid absorbent that comprises a synthetic resin film and a liquid-absorbing layer bonded via a resin adhesive therebetween requires the process of adhesive application, thereby increasing the production costs thereof. In addition, in this, if the amount of the adhesive used therein is too much, the excessive adhesive will penetrate into the liquid-absorbing layer and will retard liquid diffusion in the layer. On the other hand, if the amount of the adhesive used therein is too small, the synthetic resin film and the liquid-absorbing layer could not be sufficiently bonded in the interface therebetween and tend to form a gap therein. The gap, if formed, retards liquid diffusion in the interface between the synthetic resin film and the liquid-absorbing layer. If the liquid diffusion in the interface between them is retarded, it interferes with the liquid absorption of the entire liquid-absorbing layer, and, as a result, the drips of food tend to remain on the surface of the resin film.

Further, Japanese Examined Patent Publication (Kokoku) No. Heisei 4-70983 in which a synthetic resin film is adhered to the liquid-absorbing layer via the melted resin around the perforations formed in the resin film, is problematic in that the bonding strength between the synthetic resin film and the liquid-absorbing layer greatly varies, and, in addition, a gap is formed in the interface between the synthetic resin film and the liquid-absorbing layer to retard liquid diffusion in the interface between them.

Still further, Japanese Unexamined Patent Publication (Kokai) No. Heisei 9-86569 in which a mesh or film of synthetic resin is heat-sealed with a liquid-absorbing layer, is also problematic in that the liquid-absorbing layer is compressed by application of heat and pressure for heat-sealing the two, whereby the liquid-absorbing layer is crushed to lose bulkiness and the liquid absorption thereof is lowered. In addition, heat-sealing could not produce sufficient adhesion in the interface between the synthetic resin mesh or film and the liquid-absorbing layer, so that there is a limit to promote the liquid diffusion in the interface.

SUMMARY OF THE INVENTION

The present invention has been worked out in view of the shortcoming in the prior art set forth above. It is therefore an object of the present invention to provide a liquid absorbent comprising a liquid-absorbing layer and a synthetic resin film, in which the liquid-absorbing layer and the synthetic resin film can be firmly bonded in the interface therebetween without significantly lowering the bulkiness of the liquid-absorbing layer, and therefore the liquid diffusion in the interface can be promoted to rapidly lead the liquid applied to the surface of the synthetic resin film into the liquid-absorbing layer.

According to an aspect of the invention, a liquid absorbent comprising:

a liquid-absorbing layer of synthetic fibers by hydrophilic treatment and/or hydrophilic fibers, and a synthetic resin film bonded to a surface of the liquid-absorbing layer and having a large number of through-holes, wherein the synthetic resin film is laminated on the surface of the liquid-absorbing layer through melt extrusion thereon, and the liquid-absorbing layer and the synthetic resin film are airtightly bonded to each other.

Preferably, a portion of the resin constituting the synthetic resin film penetrates into the liquid-absorbing layer in the boundary between the liquid-absorbing layer and the synthetic resin film.

In the step of melt-extrusion lamination, when the synthetic resin film is laminated on the liquid-absorbing layer, the synthetic resin film and the liquid-absorbing layer firmly bond to each other via the interface between them, thereby increasing the density of the fibers and the resin in that interface and promoting liquid diffusion therein. Accordingly, the liquid applied to the surface of the synthetic resin film is rapidly led into the liquid-absorbing layer through the through-holes (or perforations) formed in the resin film.

Preferably, the synthetic resin film is composed of a first layer formed through melt-extrusion lamination on the surface of the liquid-absorbing layer, and a second layer formed through melt-extrusion lamination on a surface of the first layer.

In this case, it is desirable that the thickness of the second layer is larger than that of the first layer, for example, the thickness of the first layer falls between 1 $\mu$m and 30 $\mu$m and that of the second layer falls between 5 $\mu$m and 50 $\mu$m, and that the overall thickness of the synthetic resin film is at least 6 $\mu$m, more preferably at least 10 $\mu$m.

Also preferably, the density in the boundary between the liquid-absorbing layer and the synthetic resin film is higher than that in any other region of the liquid-absorbing layer.

When the synthetic resin film has a multi-layered structure, it is possible to avoid lowering the bulkiness of the underlying liquid-absorbing layer in the step of melt-extrusion lamination.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENTS

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Figure 1:
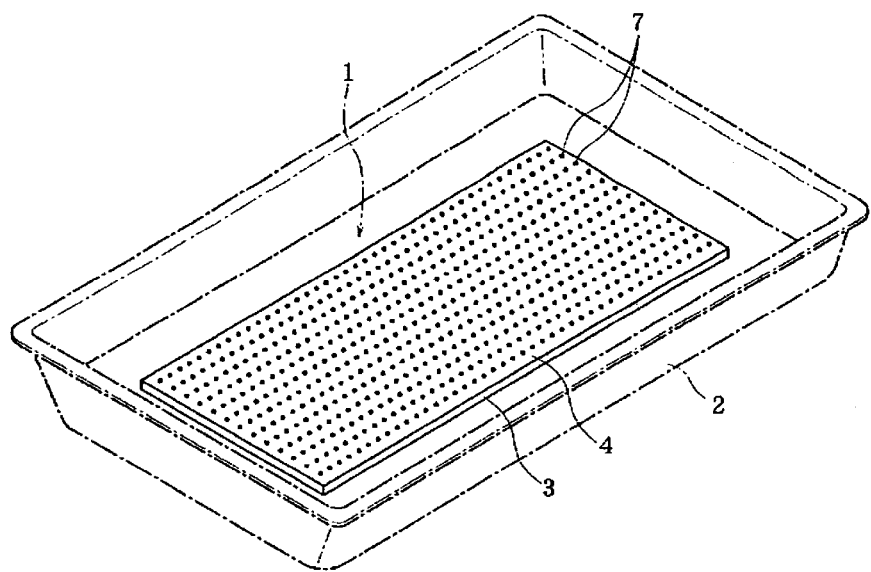
FIG. 1 is a perspective view showing one embodiment of using a liquid absorbent of the invention for a food drip-absorbing sheet.
Figure 2:
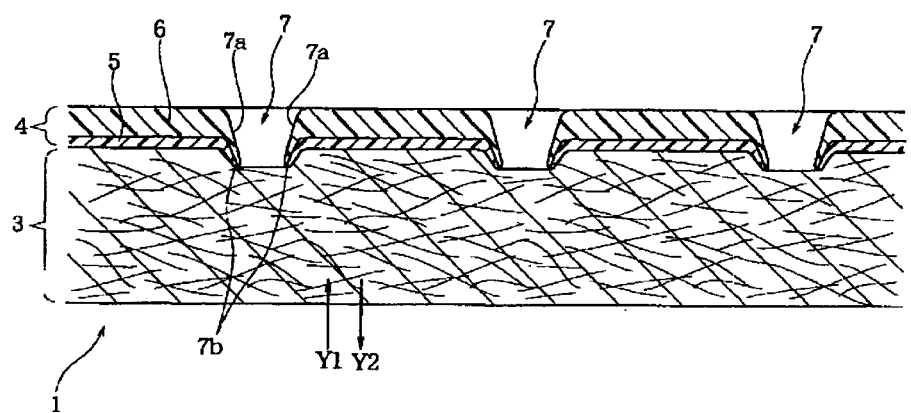
FIG. 2 is a cross-sectional view of the liquid absorbent of the invention.
Figure 3:
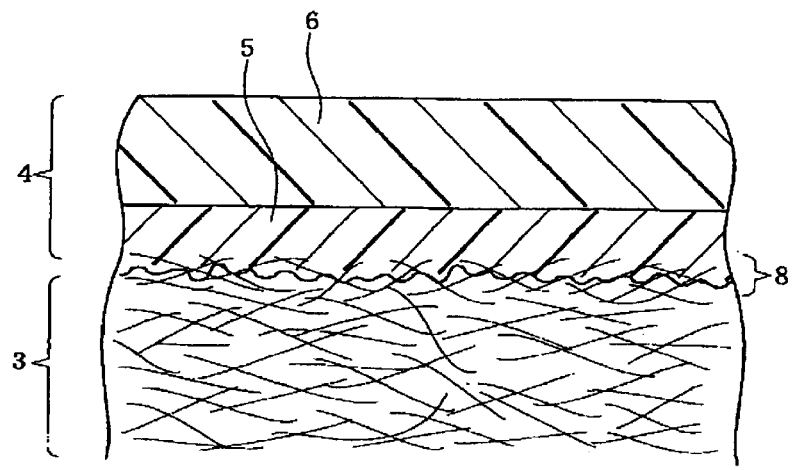
FIG. 3 is an enlarged cross-sectional view of the liquid absorbent of FIG. 2.

FIG. 1 is a perspective view showing one embodiment of using a liquid absorbent of the invention for a food drip-absorbing sheet, FIG. 2 is a cross-sectional view of the liquid absorbent, and FIG. 3 is an enlarged cross-sectional view of the liquid absorbent of FIG. 2.

As shown in FIG. 1, a liquid absorbent 1 of the invention serving as a drip-absorbing sheet is disposed in the bottom of a food tray 2, and perishable food such as raw meat or raw fish is laid on the liquid absorbent 1. In general, the upper opening portion of the food tray 2 with such perishable food therein is covered with a wrapping film to put on sale.

As shown in FIG. 2, the liquid absorbent 1 comprises a liquid-absorbing layer 3, and a synthetic resin film 4 that covers the surface of the liquid-absorbing layer 3. The synthetic resin film 4 has a laminate structure that includes a first layer 5 formed on the side of the liquid-absorbing layer 3 and a second layer 6 formed on the surface of the first layer 5. Alternatively, the synthetic resin film 4 may be composed of three or more layers.

The synthetic resin film 4 has a large number of perforations 7 serving as through-holes that pass liquid therethrough. In place of such perforations, the film 4 may have a large number of splits or slits also serving as through-holes. In the shown embodiment of FIG. 2, each perforation 7 has an inner peripheral wall 7a which is tapered off toward the liquid-absorbing layer 3. A wall end 7b of the inner peripheral wall 7a extends toward the liquid-absorbing layer 3.

The liquid-absorbing layer 3 is made of an aggregate of fibers, and is, for example, a nonwoven fabric produced in a through-air bonding process. For the constituent fibers of the nonwoven fabric, for example, used are bicomponent synthetic fibers having a core/sheath structure in which the sheath is PE (polyethylene) and the core is PP (polypropylene), for which the fibers are coated with surfactant or hydrophilic oil, or surfactant or hydrophilic oil is infiltrated thereinto for hydrophilic treatment. Also usable are a nonwoven fabric made of hydrophilic fibers, for example, natural cellulose fibers of pulp or the like, or regenerated cellulose fibers; and a nonwoven fabric made of such hydrophilic fibers and bicomponent synthetic fibers treated to be hydrophilic. Not limited to the through-air bonding process, the nonwoven fabric for use herein may be produced in any other process such as a spun-bonding process, an air laying process, a spun-lacing process, etc.

Preferably, the basic weight of the liquid-absorbing layer 3 falls between 10 g/m$^2$ and 100 g/m$^2$, more preferably between 10 g/m$^2$ and 60 g/m$^2$. Also preferably, the thickness of the layer 3 falls between 0.1 mm and 5.0 mm, more preferably between 2 mm and 5 mm. The fiber density of the layer 3 preferably falls between 0.001 g/cm$^3$ and 0.1 g/cm$^3$.

Figure 4:
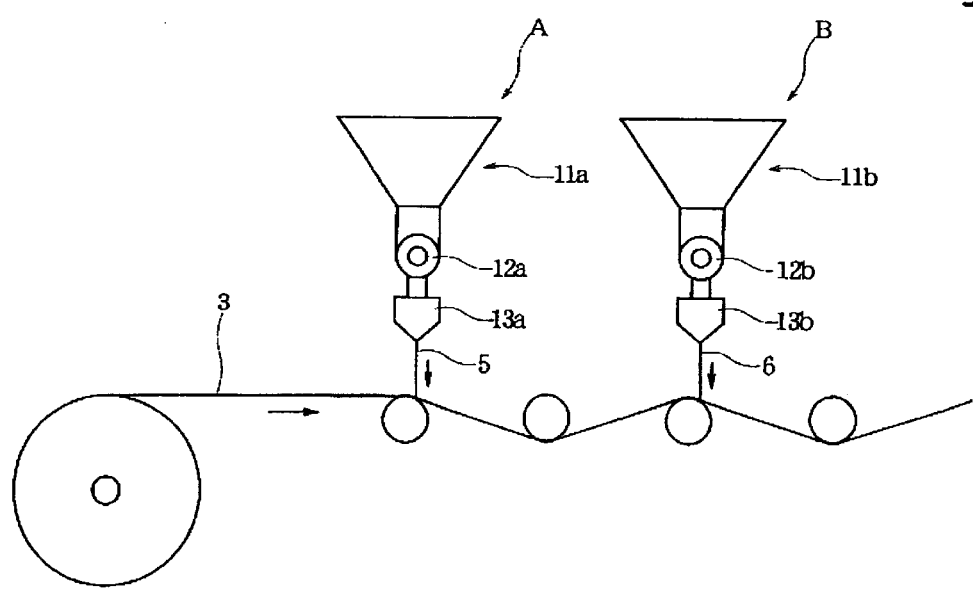
FIG. 4 is a schematic view showing one embodiment of the process of producing the liquid absorbent of the invention.

The synthetic resin film 4 is bonded to the liquid-absorbing layer 3 through melt extrusion lamination. One embodiment of producing the liquid absorbent of the invention is shown in FIG. 4. As shown in FIG. 4, a nonwoven fabric to be the liquid-absorbing layer 3 is continuously fed to a line, the first layer 5 is firstly formed on the layer 3 in a first lamination step A, and then the second layer 6 is formed on the first layer 5 in a second lamination step B.

To form the first layer 5, a resin of LDPE (low-density polyethylene) or a mixture of LDPE and HDPE (high-density polyethylene), which contains a whitening agent of an inorganic or organic filler to be added thereto, is fed from a hopper 11a into a melt extruder 12a, and its melt is extruded out through a die 13a and laminated on the liquid-absorbing layer 3.

To form the second layer 6, a resin of HDPE (high-density polyethylene) or a mixture of HDPE and LDPE, which contains an inorganic or organic filler to be added thereto, is fed from a hopper 11b into a melt extruder 12b, and its melt is extruded out through a die 13b and laminated on the first layer 5.

For the resin to form the first and second layers, also usable herein are LLDPE (linear low-density polyethylene), MDPE (middle-density polyethylene), PP (polypropylene), PET (polyethylene terephthalate), EVA (ethylene-vinyl acetate copolymer), etc. In the invention, it is desirable to combine the resins for the two layers so that the resin density of the second layer 6 is higher than that of the first layer 5.

For the inorganic filler, herein usable is any of titanium oxide, calcium carbonate, barium sulfate, etc. The filler is mixed in the resin in the range of from 0.1 to 30% by weight.

Also preferably, the first layer 5 is thinner than the second layer 6. For example, it is desirable that the thickness of the first layer 5 falls between 1 µm and 30 µm or so, and the thickness of the second layer 6 falls between 5 µm and 50 µm or so. Preferably, the overall thickness of the synthetic resin film 4 (i.e., the sum of thickness of the first and second layers) falls between 6 µm and 80 µm, more preferably between 10 µm and 80 µm.

Since a thin resin layer is laminated on the liquid-absorbing layer 3 to provide the first layer 5, it is possible to avoid lowering the bulkiness of the liquid-absorbing layer 3 in the melt-extrusion lamination step. In addition, the thin first layer 5 prevents much resin from penetrating into the liquid-absorbing layer 3 to avoid lowering the liquid absorbability of the layer 3.

Furthermore, since a thick resin layer is laminated on the surface of the first layer 5 to provide the second layer 6, the overall thickness of the synthetic resin film 4 containing the whitening agent can be thick. Accordingly, due to thick whitish resin film, it is possible to improve the effect of concealing or hiding the color of the drips such as blood absorbed by the liquid-absorbing layer 3. In addition, the thick synthetic resin film 4 increases the stiffness of the liquid absorbent 1 as a whole. Further, the thin first layer 5 makes the surface roughness of the fibrous liquid-absorbing layer 3 even, and therefore the thick second layer 6 to be formed on the first layer 5 may have a smooth surface.

In order to improve the effect of concealing the color of the drips, to ensure the stiffness of the liquid absorbent 1, and to smooth the surface of the synthetic resin film 4, the total thickness of the synthetic resin film 4 must be at least 6 $\mu$m, preferably at least 10 $\mu$m. However, if such a thick resin film having a thickness of 6 $\mu$m to 10 $\mu$m or more is laminated on the liquid-absorbing layer 3 in one step of melt extrusion, much resin will penetrate into the layer 3 to lower the liquid-absorbing ability of the layer 3. In addition, if much resin melt penetrates around the fibers constituting the layer 3, the bulkiness of the layer 3 is lowered and the liquid-absorbing ability thereof is also lowered. In this case, the liquid-absorbing layer 3 must be thicker more than necessary, thereby increasing the production costs of the liquid absorbent 1.

In the invention, however, the thin first layer 5 is firstly formed so that the amount of the resin to penetrate into the liquid-absorbing layer 3 can be reduced. Accordingly, the synthetic resin film 4 having a thickness of 10 $\mu$m or more can be formed on the liquid-absorbing layer 3 having a relatively low bulkiness.

In addition, in the invention, the synthetic resin film 4 is laminated on the surface of the liquid-absorbing layer 3 in a mode of resin melt lamination, so that the synthetic resin film 4 and the layer 3 can be airtightly bonded in the interface therebetween. Specifically, in the boundary between the liquid-absorbing layer 3 and the synthetic resin film 4, formed is a fiber-resin mixed region 8 in which the molten resin of the synthetic resin film 4 has penetrated into the fibers of the liquid-absorbing layer 3.

In particular, since the first layer 5 is thin and has a relatively low resin density, it is possible to form the mixed region 8 having a suitable thickness. Furthermore, when core/sheath bicomponent fibers of PET/PE or PP/PE in which PE forms the sheath of each fiber are used for forming the liquid-absorbing layer 3 and when the first layer 5 is formed of a polyethylenic resin, the adhesiveness between the fibers and the resin of the first layer 5 is increased in the mixed region 8. In addition, in this case, since the core of each fiber of the liquid-absorbing layer 3 is PET or PP, the layer 3 facilitates keeping the bulkiness thereof.

In the mixed region 8, the fibers constituting the liquid-absorbing layer 3 physically bond to the resin of the first layer 5 to form an anchor structure in which the fibers penetrate into the resin and vice versa. In addition, when the resin is laminated on the liquid-absorbing layer 3 in a mode of melt extrusion lamination, the oxide group in the molten resin of the first layer 5 may react with the polar group in the fibers of the layer 3 on the molecular level to form chemical bonds therebetween.

Accordingly, in the entire region of the liquid absorbent 1, the liquid-absorbing layer 3 and the synthetic resin film 4 are uniformly bonded in their interface. Furthermore, in the mixed region 8, no excessive space is formed in the mixed region 8 and the fibers and the resin are mixed therein. As a result, the density of the fibers and the resin in the mixed region 8 is higher than in any other region of the layer 3 to facilitate liquid diffusion. Specifically, the molten resin of the synthetic resin film 4 penetrates into the fibers of the liquid-absorbing layer 3 to reduce the space between the fibers. Accordingly, there is a limited amount of space between the fibers for causing capillary action in the mixed region 8. Owing to such capillary action, the mixed region 8 can serve as the layer for promoting liquid permeation and diffusion in the layer 3.

After the synthetic resin film 4 has been laminated on the liquid-absorbing layer 3, a large number of needles are pushed into the laminate structure in the direction Y1 (shown in FIG. 2) to pass through the synthetic resin film 4, and then the needles are drawn away in the direction Y2 (shown in FIG. 2). In that manner, formed are perforations 7 of which the wall ends 7b extend on the side of the liquid-absorbing layer 3, as shown in FIG. 2.

The needles may be at room temperature or may be heated. Preferably, the diameter of each perforation 7 falls between 0.2 mm and 5.0 mm; the perforation pitch falls between 1.0 mm and 10 mm; and the perforation area ratio falls between 0.3% and 5.0%. Within the defined ranges, liquid can be readily led into the liquid-absorbing layer 3 through the perforations 7, and, in addition, the synthetic resin film 4 facilitate concealing the liquid such as blood absorbed by the liquid-absorbing layer 3.

In the liquid absorbent 1, the food drips such as blood having been applied to the surface of the synthetic resin film 4 are led into the perforations 7, and sucked into the liquid-absorbing layer 3 owing to capillary action between the fibers of the layer 3. Owing to such suction force, the drips on the surface of the synthetic resin film 4 are lead into the liquid-absorbing layer 3. The drips thus having been led into the liquid-absorbing layer 3 through the perforations 7 are rapidly diffused in the mixed region 8 in the interface between the layer 3 and the synthetic resin film 4. Having been thus diffused, the drips on the surface of the synthetic resin film 4 are rapidly absorbed by the liquid-absorbing layer 3 to avoid remaining thereon.

In the liquid absorbent of the invention, the liquid applied to the surface thereof diffuses in the mixed region 8 in the interface between the layer 3 and the film 4, as set forth above. Therefore, even though the liquid-absorbing layer 3 is not so thick, it can rapidly absorb the liquid on the surface of the synthetic resin film 4. The reasons for ensuring such rapid liquid diffusion in the mixed region 8 are as follows.

(1) Since the synthetic resin film 4 is formed on the liquid-absorbing layer 3 in a mode of melt-extrusion lamination, the adhesiveness between the film 4 and the layer 3 is increased in the boundary therebetween. Therefore, no gap is formed in the boundary to ensure increased liquid diffusion in the interface between the film 4 and the layer 3.

(2) In the mixed region 8, the resin of the resin film 4 penetrates into the fibers of the liquid-absorbing layer 3, and therefore the density of the fibers and the resin in the mixed region 8 is higher than in any other region of the layer 3. Accordingly, owing to capillary action in the mixed region 8, the liquid applied to the absorbent 1 rapidly diffuses along the boundary between the film 4 and the layer 3.

(3) When the synthetic resin film 4 is formed on the liquid-absorbing layer 3 through lamination, the surfactant or hydrophilic oil contained in the fibers of the layer 3 dissolves out and adheres to the interface of the film 4 in the mixed region 8. As a result, the interface of the film 4 acts to lead liquid into the layer 3.

Accordingly, the liquid absorbent 1 of the invention ensures excellent liquid diffusion and absorption therein even though it is thin, and the drips on the surface of the synthetic resin film 4 can be removed almost completely. To that effect, the liquid absorbent of the invention is extremely effective for ensuring the freshness of perishables laid thereon and for ensuring the commercial value of packaged perishables.

Similarly, in case where the liquid absorbent 1 is used for sanitary napkins or pantiliners, it prevents the body discharges from remaining on the surface thereof, and does not give a wet feel to wearers. Accordingly, it is possible to provide thin absorbent articles having good capabilities of liquid absorption and diffusion.

EXAMPLES

The invention will be described in more detail with reference to the following Examples, which, however, are not intended to restrict the scope of the invention.

Example 1

For providing the liquid-absorbing layer 3, hydrophilic oil-coated, core/sheath-structured bicomponent synthetic fibers in which the core is PET and the sheath is PE were formed into a nonwoven fabric having basic weight of 30 g/m$^2$, according to a through-air bonding process.

The synthetic resin film having a two-layered structure was provided. For the first layer 5, a film composed of LDPE and titanium oxide (TiO$_2$) in a ratio of 85:15 (% by weight) and having a thickness of 7 μm was laminated on the liquid-absorbing layer 3, in a mode of melt-extrusion lamination. For the second layer 6, a film composed of HDPE, LDPE and titanium oxide in a ratio of 75:10:15 (% by weight) and having a thickness of 13 μm was further laminated on the first layer 5, in a mode of melt-extrusion lamination.

A large number of perforations 7 were arranged at a pitch of 4 mm both in the longitudinal direction and the transverse direction of the film. The diameter of each perforation was about 0.4 mm, and the perforation area ratio thereof was 1.0%.

Example 2

The synthetic resin film having a single-layered structure was provided. The same first layer 5 as in Example 1 was laminated on the same liquid-absorbing layer 3 as in Example 1, in a mode of melt-extrusion lamination. The resin film has a thickness of 20 μm. A large number of perforations 7 were formed in the same manner as in Example 1.

Comparative Example 1

For providing Comparative Example 1, the same liquid-absorbing layer 3 as in Example 1 was not laminated with a resin film.

Comparative Example 2

For providing Comparative Example 2, a resin film of LDPE having a thickness of 20 μm was point-bonded to the same liquid-absorbing layer 3 as in Example 1, by use of a hot melt adhesive. A large number of perforations 7 were formed in the same manner as in Example 1.

Liquid Diffusion Test

The samples of Example 1, Comparative Example 1 and Comparative Example 2 were cut into square pieces of 80×65 mm. 1 cc of a colored physiological saline solution was dropped onto the surface of each piece of the samples. After 1 minute, the two-dimensional size of the diffusion area of the solution in the liquid-absorbing layer 3 of each piece was measured. The obtained data are given in Table 1 below.

TABLE 1

|  | Example 1 | Com. Example 1 | Com. Example 2 |
| --- | --- | --- | --- |
| Diffusion Area | 80 × 65 mm (diffused everywhere in the layer) | 45 × 35 mm | 46 × 36 mm |

Evaluation of Liquid-absorbing Layer

The sample of Example 1 laminated with the two-layered synthetic resin film 4 was compared with that of Example 2 laminated with the single-layered synthetic resin film 4 in point of the bulkiness and the water capacity (for this, used was a 0.9% physiological saline solution). The obtained data are given in Table 2 below.

TABLE 2

|  | Example 1 | Example 2 |
| --- | --- | --- |
| Bulkiness | 0.504 mm | 0.280 mm |
| Water Capacity | 356 g/m$^2$ | 181 g/m$^2$ |

As set forth above, the liquid absorbent of the invention is excellent in the capability for liquid absorption and diffusion, even though it is thin. When it receives liquid, little liquid remains on the surface of the resin film. In addition, it does not require a step of bonding the constituent layers to reduce the production costs thereof.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A liquid absorbent comprising:

a liquid absorbing layer having a liquid absorbing fibrous structure;

a first synthetic resin film formed on one surface of said liquid absorbing layer;

a second synthetic resin film formed on said first synthetic resin film;

said first synthetic resin film and said second synthetic resin film having a large number of through holes, and a thickness of said second synthetic film being larger than that of said first synthetic film;

said first synthetic resin film having a smaller resin density than that of said second synthetic resin film and partially penetrating into said fibrous structure forming said liquid absorbing layer for forming an interfacial layer lying between said first synthetic resin film and said liquid absorbing layer for joining therebetween and blocking penetration of a second synthetic resin material forming said second synthetic resin film into said fibrous structure of said liquid absorbing layer to avoid reducing a liquid absorbability of said liquid absorbing layer.

2. A liquid absorbent comprising:

a liquid absorbing layer having a liquid absorbing fibrous structure;

a first synthetic resin film formed on one surface of said liquid absorbing layer having a thickness in a range of 1 to 30 $\mu$m;

a second synthetic resin film formed on said first synthetic resin film having a thickness in a range of 5 to 50 $\mu$m so as to form a synthetic resin film consisting of said first and second synthetic resin films in a thickness in a range of 6 to 80 $\mu$m;

a thickness of said second layer being larger than that of said first layer;

said first synthetic resin film having a smaller resin density than that of said second synthetic resin film and partially penetrating into said fibrous structure forming said liquid absorbing layer for forming an interfacial layer lying between said first synthetic resin film and said liquid absorbing layer.

3. A liquid absorbent comprising:

a liquid absorbing layer having a liquid absorbing fibrous structure;

a first synthetic resin film formed on one surface of said liquid absorbing layer having a thickness in a range of 1 to 30 $\mu$m;

a second synthetic resin film formed on said first synthetic resin film having a thickness in a range of 5 to 50 $\mu$m so as to form a synthetic resin film consisting of said first and second synthetic resin films in a thickness in a range of 6 to 80 $\mu$m;

a thickness of said second layer being larger than that of said first layer;

said first synthetic resin film having a smaller resin density than that of said second synthetic resin film and partially penetrating into said fibrous structure forming said liquid absorbing layer for forming an interfacial layer lying between said first synthetic resin film and said liquid absorbing layer for joining therebetween and blocking penetration of a second synthetic resin material forming said second synthetic resin film into said fibrous structure of said liquid absorbing layer to avoid reducing a liquid absorbability of said Liquid absorbing layer.

* * * * *